US007013365B2

(12) United States Patent
Arnouse

(10) Patent No.: US 7,013,365 B2
(45) Date of Patent: Mar. 14, 2006

(54) SYSTEM OF SECURE PERSONAL IDENTIFICATION, INFORMATION PROCESSING, AND PRECISE POINT OF CONTACT LOCATION AND TIMING

(76) Inventor: Michael Arnouse, 15 Hickory Dr., Old Brookville, NY (US) 11545

(*) Notice: Subject to any disclaimer, the term of this patent is extended or adjusted under 35 U.S.C. 154(b) by 353 days.

(21) Appl. No.: 10/462,532

(22) Filed: Jun. 16, 2003

(65) Prior Publication Data

US 2004/0255081 A1    Dec. 16, 2004

(51) Int. Cl.
*G06F 12/14*    (2006.01)

(52) U.S. Cl. .................................... 711/115; 711/163
(58) Field of Classification Search ............. 711/115; 235/441–449
See application file for complete search history.

(56) References Cited

U.S. PATENT DOCUMENTS

| | | | |
|---|---|---|---|
| 3,655,947 A | 4/1972 | Yamamoto et al. | |
| 3,778,595 A | 12/1973 | Hatanka et al. | |
| 4,164,320 A | 8/1979 | Irazoqui et al. | |
| 4,839,857 A | 6/1989 | Mersiovsky et al. | |
| 4,959,788 A | 9/1990 | Nagata et al. | |
| 5,229,764 A | 7/1993 | Matchett et al. | |
| 5,548,566 A | 8/1996 | Barker | |
| 5,652,570 A | 7/1997 | Lepkofker | |
| 5,751,246 A | 5/1998 | Hertel | |
| 5,832,488 A | 11/1998 | Eberhardt | |
| 5,859,416 A | 1/1999 | Gatto | |
| 5,987,136 A | 11/1999 | Schipper et al. | |
| 5,995,936 A | 11/1999 | Brais et al. | |
| 6,027,216 A | 2/2000 | Guyton et al. | |

(Continued)

FOREIGN PATENT DOCUMENTS

CA    2220035    5/1995

(Continued)

OTHER PUBLICATIONS

Motorola Press Release, Motorola Unveils Latest in Family of Single Chip GPS Device, Sep. 24, 2002 http://www.motorola.com/mediacenter/news/detail/0,1958,1888_15 14_23,00.html.*

(Continued)

*Primary Examiner*—Mano Padmanabhan
*Assistant Examiner*—Daniel Ko
(74) *Attorney, Agent, or Firm*—DLA Piper Rudnick Gray Cary US LLP

(57) ABSTRACT

A universal lightweight, easily carried memory identification card records information and controls access to this information. The memory card includes a file system of electronic files on the card, which are automatically detected and recognized by selected authorized readers. The file system is organized so that stored electronic files appear in separate and distinct encrypted compartments in the card, so that only authorized preselected readers have access to particular compartments. Biometric identifying information is imprinted in the card, so that no data can be transferred unless there is a biometric match between a reader and a person assigned to the card and who possesses the card. The separate compartments of the memory card may include a compartment containing medical, administrative or financial information relating to the assigned user of the card, wherein the information is accessed only by a preselected memory card reader having the unique pin code assigned to the compartment having the medical information. The memory identification card can also have a single chip Global Positioning System (GPS) to identify where the card is being used.

34 Claims, 9 Drawing Sheets

U.S. PATENT DOCUMENTS

| | | |
|---|---|---|
| 6,078,848 A | 6/2000 | Bernstein et al. |
| 6,079,621 A * | 6/2000 | Vardanyan et al. .......... 235/487 |
| 6,104,809 A | 8/2000 | Berson et al. |
| 6,131,090 A | 10/2000 | Basso, Jr. et al. |
| 6,140,936 A | 10/2000 | Armstrong |
| 6,144,848 A | 11/2000 | Walsh et al. |
| 6,205,437 B1 | 3/2001 | Gifford |
| 6,219,439 B1 | 4/2001 | Burger |
| 6,224,109 B1 | 5/2001 | Yang |
| 6,259,769 B1 | 7/2001 | Page et al. |
| 6,282,154 B1 | 8/2001 | Webb |
| 6,304,848 B1 | 10/2001 | Singer |
| 6,333,988 B1 | 12/2001 | Seal et al. |
| 6,378,774 B1 * | 4/2002 | Emori et al. ................. 235/492 |
| 6,386,451 B1 | 5/2002 | Sehr |
| 6,421,650 B1 | 7/2002 | Goetz et al. |
| 6,445,300 B1 | 9/2002 | Luman |
| 6,446,335 B1 * | 9/2002 | Carlson et al. ................ 29/861 |
| 6,450,407 B1 | 9/2002 | Freeman et al. |
| 6,463,039 B1 | 10/2002 | Ricci et al. |
| 6,493,672 B1 | 12/2002 | D'Agosto, III et al. |
| 6,510,380 B1 | 1/2003 | Curatolo et al. |
| 6,522,552 B1 | 2/2003 | Lee |
| 6,546,112 B1 | 4/2003 | Rhoads |
| 6,557,752 B1 | 5/2003 | Yacoob |
| 6,759,738 B1 * | 7/2004 | Fallon et al. ................ 257/690 |
| 2001/0018639 A1 | 8/2001 | Bunn |
| 2002/0035484 A1 | 3/2002 | McCormick |
| 2002/0084904 A1 * | 7/2002 | De La Huerga ......... 340/573.1 |
| 2002/0084915 A1 | 7/2002 | Budnovitch |
| 2002/0095587 A1 | 7/2002 | Doyle et al. |
| 2002/0100803 A1 | 8/2002 | Sehr |
| 2002/0116575 A1 * | 8/2002 | Toyomura et al. .......... 711/115 |
| 2002/0118112 A1 | 8/2002 | Lang |
| 2002/0190121 A1 * | 12/2002 | Walker et al. .............. 235/380 |
| 2003/0017871 A1 | 1/2003 | Urie et al. |
| 2003/0052159 A1 | 3/2003 | Kawan |
| 2003/0150915 A1 * | 8/2003 | Reece ........................ 235/449 |
| 2004/0153601 A1 * | 8/2004 | Blankenagel ............... 711/103 |
| 2004/0210715 A1 * | 10/2004 | Harari et al. ............... 711/115 |
| 2005/0086421 A1 * | 4/2005 | Nassar ........................ 711/103 |
| 2005/0198433 A1 * | 9/2005 | Kobayashi et al. .......... 711/112 |
| 2005/0216685 A1 * | 9/2005 | Heden et al. ................ 711/163 |

FOREIGN PATENT DOCUMENTS

| | | |
|---|---|---|
| EP | 1004980 A2 | 5/2000 |
| EP | 1073025 A2 | 1/2001 |
| FR | 2791091 A1 | 10/2000 |
| FR | 2798208 A1 | 3/2001 |
| JP | 7319983 A2 | 12/1995 |
| WO | WO 97/22092 | 6/1997 |
| WO | WO 03/015299 A1 | 2/2003 |

OTHER PUBLICATIONS

"Motorola Automotive Announces Revolutionary Single Chip GPS Device," Motorola Press Release; Farmington Hills, Michigan; Sep. 23, 2002.

"Instant GPS" Motorola Brochure; Framington Hills, Michigan; 2002.

* cited by examiner

SYSTEM OF SECURE PERSONAL IDENTIFICATION, INFORMATION PROCESSING, AND PRECISE POINT OF CONTACT LOCATION AND TIMING

FIELD OF THE INVENTION

The present invention relates generally to information and more particularly to methods of information processing, which will make identity theft obsolete.

BACKGROUND OF THE INVENTION

Signatures have been utilized for centuries as the primary method of authentication. For many years, the process has involved a visual inspection between a newly signed document and a prior signature. This process, however, has significant limitations, as it typically depends on subjective decisions made by individuals having little skill, if any, in making signature comparisons. In recent years, computers have been increasingly utilized to assist in the authentication process, however, there are still significant drawbacks. Much of the problems have been a result of the increased globalization of business and society. For example, differences in language, culture and geographic location have added many new variables that have needed to be considered and dealt with appropriately.

Another complicating factor is that we live, it is said, in the 'information age'. What is meant by that phrase is that we live in a time when information is very important and easily accessible. To get a real appreciation, however, as to the impact the information age has had on society, it is necessary to reflect on the meaning of term "information" itself. "Information" is a term that has broad implications in today's environment and covers any type of "data" or "facts" and in any format, such as, for example, text, graphics, audio or video, to name a few.

Technological innovation has made it progressively easier in recent years to disseminate information from place to place, for example, by telephone, portable devices, such as recorders or PDA's, and via computer networks, such as the internet. The ease by which information can be readily obtained and disseminated have raised many concerns, such as privacy issues as well as issues of fraud and security concerns. Laws have been enacted in attempt to deter piracy of sensitive public or private information, but that has done little to address the source of the problem.

Moreover, as technology advances and links goods and services throughout the world, the economy and stability of civilized societies become more vulnerable to sophisticated means of attack and destabilization. Government and businesses are linked world wide via telephone, cable, and wireless technologies. This technological communications revolution has left our society open to a new worldwide threat. Interference with our current technologies by a third party wishing to cause chaos in the free world is a constant and real threat to all people.

The computer linked worldwide communications systems are vulnerable based on the current system. The present system allows acceptance of devastating electronic programs such as so called "worms" and "viruses". The present system also allows the very worrisome intrusion by "hackers", who can gain control of vital government functions and an individual's personal records.

Apart from prevention of attacks upon the information that is linked to government and private institutions, a method to track and help apprehend the criminals and terrorists that wish to harm the free world is also needed. Presently, there is no system in place to link the actual person responsible for the attack to the crime.

In view of the forgoing, there is seen a need for improving the manner by which information integrity can be maintained and dissemination regulated.

SUMMARY OF THE INVENTION

The present invention discloses a system and method of information processing.

In accordance with one embodiment, a method comprises the steps of storing information in a memory device and regulating access to the information stored in the memory device based upon a security measure. In an exemplary embodiment, the security measure may comprise one or more biometric characteristics. The method may further comprise one or both of the steps of providing a reader to regulate access to the information stored in the memory device and providing an interface to communicate with the reader or memory device upon permission to access the information. The method may also comprise the step of identifying the location of the memory device at desired times.

BRIEF DESCRIPTION OF THE DRAWINGS

The present invention can best be understood in connection with the accompanying drawing, in which.

DETAILED DESCRIPTION OF THE INVENTION

The following embodiments of the present invention may be implemented using hardware or software or any combination of the two where desired. Various embodiments may also be implemented using commercially available technology.

In one embodiment, a system for processing information comprises the steps of storing information and regulating access to the information based upon a security measure. In an exemplary embodiment, the security measure may comprise one or more biometric characteristics, which is described in further detail below, although it should be understood that any desired security measure may be utilized where desired.

Figure 1:
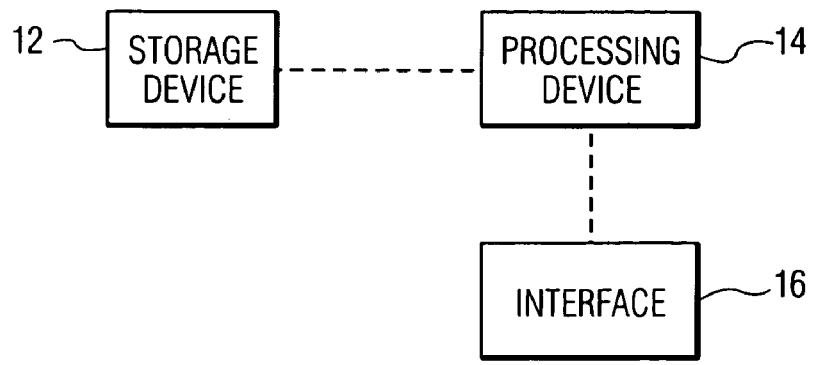
FIG. 1 is a block diagram illustrating an exemplary embodiment of the present invention.

In order to illustrate the foregoing system, the following example is provided comprising a storage device 12, such as an identification memory card, a processing device 14, such as an identification card reader, and an interface 16, such as a host device, as is illustrated in FIG. 1.

The term "storage device" as used herein should be broadly construed to comprise any device that includes the capability of storing information, such as via any suitable electronic or magnetic storage medium adapted for storing information in digital and/or analog form. The term "identification memory card" should also be broadly construed to comprise any storage device suitably sized and configured so as to be portable. For purposes of illustration, the following examples are described in relation to one embodiment of an identification memory card comprising a smart card type of device, such as a Digital ID™ ("DID™") card, which is preferably sized and configured corresponding to a conventional credit card and includes memory and processing capabilities to store and process information in digital form. It should be understood, however, that the identification memory card may comprise other sizes and configurations where desired as well as store and process information in other formats, such as analog and/or magnetic, to name a few.

The term "processing device" as used herein should be broadly construed to comprise any device having the capability for communicating with the storage device and interface described herein and for processing information relative to these devices where desired. The term "identification memory card reader" as used herein should also be broadly construed to comprise any suitable type of processing device capable for communicating with the identification memory card and host device in accordance with embodiments of the present invention, such as is illustrated in FIG. 1 and described in detail below.

The terms "interface" and "host device" as used herein should be broadly construed to comprise any suitable device adapted for communicating with the processing device/identification memory card reader and/or the storage device/identification memory card, where desired. For example, the host device may comprise a separate device, such as a computer or telephone or any other suitable device, capable of interfacing with the identification card reader. This interface may be accomplished by any suitable, means, such as via standard Serial, USB, or IEEE-1394 "firewire" computer interfaces. In other embodiments, the host device and identification card reader may comprise a single device. Application software may run on the host computer for any number of given services, such as commercial transactions, medical records, travel documents, entertainment transactions, government administrative documents and the like. Each service may have distinct application software as well as a unique identification reader/sender associated with it for reading and transacting the transactions of the identification memory card. The host computer gains access to the identification card data through interface with the identification card reader, which in one embodiment includes a user-specific biometric keying device on it. The identification card reader sends the biometric data to the host computer for later processing and comparison. The reader may be unique for other applications. Different applications may access different encrypted areas of the identification card's secure memory where desired.

The term "computer" as used herein, includes any device capable of receiving, transmitting, and/or using information, including, without limitation, a processor; a microprocessor; a personal computer, such as a laptop, palm PC, desktop or workstation; a network server; a mainframe; an electronic wired or wireless device, such as for example, a telephone; an interactive television or electronic box attached to a television, such as for example, a television adapted to be connected to the Internet; a cellular telephone; a personal digital assistant; an electronic pager; and a digital watch.

As will be described in more detail below, in accordance with various embodiments of the present invention, information may be transferred between the storage device/memory card 12 and one or more locations external to the storage device/memory card 12. The term "one or more locations" should be broadly construed to comprise any designated location that is desired to interact with the storage device/memory card 12, such as an institution as an example, as is descussed below. The one or more external locations may include one or more databases or similar types of storage devices capable of interacting with the storage device/memory card 12 by uploading and downloading of the information.

Information may be transferred between the storage device/memory card 12 and the various external locations via the processing device/identification memory card reader 14 and/or interface/host device 16, for example, over any network, such as, for example, any wired or wireless network, such as a telephone or cellular telephone network, the Internet, an intranet, or an extranet.

In one embodiment, for example, although others are applicable as well, the reader may have a configurable contact or pin arrangement that provides for each reader being unique for a given application. In this way, different readers may be needed for access to different areas of the identification card memory. The identification card reader may contain an AC or DC power source and a controller interfacing with the identification card. Furthermore, location tracking may also be incorporated into the overall system where desired. For example, the reader may be equipped with required front end RF and conversion needed to support a single chip receiver and a global positioning system (GPS) processor in the identification card.

In another embodiment, the identification card may contain a configurable contact or pin arrangement that is decoded for access to the secure memory of the identification card. In this way, application data contained in the memory for one purpose preferably will not be accessed by another unrelated application intended for another purpose. For example, a provider of medical records cannot have access to commercial banking records, and vice versa. In this manner, access to the data is restricted and tailored for one use or another. Identification card memory may be segmented by each application area. Each area may also be assigned a designated capacity space for storage. These information areas may include, but are not necessarily limited to, one or more of the following examples: encrypted data of an identification card carrier, photographs, medical history, credit card information, dental records, driver information, credit card records, immigration documents, travel and passport records and general personalized data, etc. Furthermore, the identification card may be equipped with a global positioning system capable device that may be powered from the identification card reader where necessary. An RF feed may be utilized when the device contained on the card, such as an onboard processor, cannot receive energy from an onboard antenna.

An exemplary embodiment may be used as a digital identification device. The digital identification device may comprise a card or like type of device that may be utilized as a secure personal information medium. In this embodiment, non-removable, non-volatile solid state memory, such as flash memory, may be used to store encrypted digital data in the record unit, although other storage mechanisms may also be utilized where desired. The memory may be partitioned and adapted to store specific data types in specific locations in the memory. In this way, memory blocks may be assigned to information areas such as, for example, personal name, encoded digital individual identifying photograph, medical history data, driver's data, etc. The card may also have a connector, such as along its bottom surface, which interfaces with a separate reader, such as a playback/send reader unit, when the card is inserted into a recessed port, such as in the reader's top surface. The playback/send unit may also have a unique pin code, which allows access to the specific data encoded on the digital identification memory card. In this manner, only specific users can gain access to specific data, making the card unalterable by others. For example, it can be regulated so that the individual who is issued the card, i.e., the owner of the card, can not access the data to tamper with or change any information, police can access the Picture ID and driver's data but not the medical or other personal data, likewise a doctor can access the medical history but not bank records, etc.

As indicated earlier, a location tracking mechanism, such as a single chip GPS engine or any other suitable device, can also be included as a part of the overall system and method. In one embodiment, when connected to the playback/send unit, an electrical path is created that connects the Antenna on the playback/send card reader unit to the single chip GPS solution. Power is then applied via the playback/send unit. Upon power-up and a time delay needed for the GPS signal to be processed, time and location information is available. This location and time information may also be used to time stamp designated or every transaction in the digital identification card. Furthermore, the playback/send unit may also contain a biometric fingerprint reader that allows correlation from user to stored biometric information on the card. Only a correct match will allow access to data on the card.

Another embodiment comprises a digital identification memory card with Wireless connectivity. In this embodiment, the digital identification memory card may be mated with wireless transmission capability. In this embodiment, the digital identification memory card may be enhanced with microprocessor, RF receive, RF transmit and a power source, such as a battery. This capability allows for connectivity to wireless LAN as well as the Internet via wireless Internet connection. Reception and decoding of the (GPS) enables the card to locate itself. In this way the location of the card can be broadcast, received and shown on a map using a standard Internet browser. Also short messaging service (SMS) or enhanced messaging service (EMS) or other text messages can be sent to a wireless mobile handset upon request of authorized user. In this embodiment, the playback/send unit may also operate as a battery charger.

In another embodiment, a location device can be provided on the memory card and may communicate by wireless means with a reader in the form of a scanner, when the card is brought into proximity with the scanner. For example, the location device can be adapted to transmit designated information, such as an ID, to the scanner either automatically or upon request of the scanner. The location device may be powered by either a source external the card, such as by the scanner, when the card is brought into proximity with the scanner, or by a power source located on the card itself. In this embodiment, the location device may be adapted to communicate with the scanner from various distances, such as directly next to one another, i.e., 0–1 foot or from larger distances, such as the size of a room or building or a complex, etc. The scanner may further process the information received from the card in any desired manner. For example, the scanner may be utilized as a counter, such as to count the number of passerby's, such as for use at stores, conventions, trade shows, etc. In addition, the scanner may compare the ID against designated information, for example, an allow/deny list, most wanted list, etc. The designated information may be stored local at the scanner or provided from an external storage source, such as via a network connection. The scanners may be located at various preselected locations, such as at border check points or other secured areas, and in radar or other law enforcement equipment, etc.

Still another embodiment is utilized as a personal digital voice recorder for persons, including but not limited to medical patients and children. In this embodiment, the recorder stores real time voice data, such as non-volatile memory. Recording may start at any desired times, such as by a parent, utilizing the playback/send unit. The recorder may then be attached to a user, such as a child or patient, and all proximity sound to the child or patient is recorded until either a low power condition or a memory full condition is reached. The memory may be scalable according to the amount of recording time and fidelity desired by the parent or authorized custodial person.

Another embodiment may be utilized as an automatic voice notebook, such as for health care professionals on rounds as an example. Similar uses, such as by building inspectors, maintenance or security and Military personnel, as an example, are also anticipated. In this embodiment, memory, such as non-removable, non-volatile memory, such as flash memory, may be used to store encrypted digital data in the record unit. A small cell may be used in this unit to keep size and weight to a minimum. A real-time clock may be embedded in the record unit to be used for time stamping the recorded voice segments. The record unit may have a connector, such as along its bottom surface, which interfaces with a separate playback unit, such as when the record unit is inserted into a recessed opening in its top surface. The playback unit may include conventional features, such as speaker, play button, volume control and "forward/reverse" switch for navigating within the data. Both the record unit and the playback unit may further have identifying features, such as matching bar codes on their housings, which can be used to identify the individual units in case of loss or to confirm identity.

A further embodiment pertains to a method and system of authentication and tracking of the personal originator of electronic files. This method enhances security and provides accountability for files such as electronic mail and electronic commercial documents to name a few. The unique personal identifier such as one or more biometric parameters are used in place of a traditional signature or written mark. This method utilizes new technology that makes use of a compact portable electronic storage device, unique identifying personal markers, such as biometrics and other personal characteristics, special tracking circuits with global positioning satellite technology, software, and any internetworking or linking of communication devices such as computers, PDA's cell phones, etc. This method further utilizes a designated unique reader to interpret the digitized data and authenticate the data by using one or more biometric sensors. This method also provides for a unique identifying mark visible "on the outside" of the file that verifies the identity of the sender of the file before the file is opened and potentially downloaded onto the recipients hard drive. The method thus allows for personal authentication and accountability as well as the exact place and time of file origination. Some exemplary advantages and embodiments of this method are listed below.

Security—the originator of the file is identified. Forgery and fraud utilizing electronic documents can be eliminated. This applies to all aspects of business including commercial and government.

Safety—the authenticated signature is visible without opening the electronic file. This method allows individuals, businesses, and government to automatically reject all files without an external authentication mark. This will make passing and spreading of harmful electronic programs such a "worms" and "Viruses" much more difficult.

Location—this system allows for location tracking either in real time or by specific event. This is done using GPS technology and software. Not only can the location be generally discovered but the exact place, time, and person can be discovered and brought to justice. Specific areas and people can be watched by authorities more closely and apprehended.

Privacy—this method allows the individual to chose what files are sent to his or her computer or device. This will effectively regulate "spam" and the invasion of an individual's privacy.

EXAMPLE A

Home Use

User I—DID™ Card placed in reader "HOME USE"—fingerprint and/or retinal scan confirmation confirms identity—electronic file is written and sent from "HOME" computer—Recipient computer receives electronic file into IN BOX—User 2 opens computer and views IN BOX—User 2 identifies an "AUTHENTICATION MARK" verifying the identity of the sender—User 2 opens the file and reads content safely and securely.

The procedure may be utilized over any computer network, such as the Internet. In addition, the procedure may be utilized in a similar manner for any person to person or multiple party communication in real time, such as instant messaging or chat room communication.

Alternatively, User 2 may pre-program his computer to only allow "Authenticated" signed files. This will automatically block most "spam" before it reaches the IN BOX. This protects the individual's privacy.

EXAMPLE B

Illegal Activity

User I—logs onto internet without secure authentication—sends file with a new virus to GOVERNMENT or BANK computer—Recipient computer software checks for Authentication Seal—No biometric seal is indicated—file automatically deleted—return message to computer originator stating no personal authorization so file was deleted without being read.

This example demonstrates a security level to help protect business and government files from attack by viruses, worms and hackers trying to hide their identity. The integrity of the organizations computer network will be safer.

EXAMPLE C

Identifying and Tracking Wrongdoers

User I—DID™ Card placed in reader—biometric sensor verifies ownership using fingerprint and or retinal scan for example—time and place stamped via GPS chip—electronic file with NEW VIRUS is created and sent to bank—bank computer opens file and becomes infected—User 1 is identified as John Doe residing at 123 Smith Lane Hollywood Calif. 99201. The file originated at (exact location and time and date)—the bank blocks all further email authenticated from User 1 biometric signature—the authorities quickly find and arrest the wrongdoer—his DID™ Card documented the transaction and is used as evidence in his trial. Similarly, the system can be utilized to prevent child pornography.

In an alternative version, the DID™ Card can be real time tracked via GPS and the criminal located faster.

In a further embodiment, the memory card may be utilized as a means to conduct various financial transaction, such as cash withdrawals or transfers as well as check or credit card transactions, to name a few. For example, in a cash transaction, the memory card may be utilized to reach a designated banking institution, such as over a network, for instance, the Internet, to electronically transfer funds from a specified account so as to be downloaded and stored on the memory card. In this embodiment, the memory card becomes, in essence, a secure wallet. Funds may also be transferred from other institutions or individuals to a particular memory card.

In a similar manner, funds may be transferred in the opposite direction from a memory card to a designated financial institution, such as for deposit, or to some non-financial institution or an individual, such as for a purchase or payment.

Also, in a check transaction, the same process can follow in that a check may be stored on the card, and when connection is made to a designated institution, the checking information may be uploaded from the card and download at the institution, such as for deposit or to make a purchase or payment by check, or the transaction may be for check cashing, in which the further step may occur of funds in electronic form being transferred from the institution and downloaded onto the card.

In the present embodiment, since funds are transmitted and received coded according to a biometric, individuals, government and businesses may freely distribute funds over the Internet, such as employee payroll. In addition, should an owner ever lose or misplace his or her card, any funds that may have been be stored on that original card are not lost. A person finding the lost card can not access the funds, since there will not be a biometric match. The same funds can then be provided on a new card by the bank, institution or party that issued the funds originally. The original funds that were issued may also be voided where desired.

Another embodiment in accordance with the present invention pertains to signature verification. As is illustrated in FIG. 1, an exemplary embodiment comprises a storage device in the form of a memory card 10, a processing device in the form of a reader 12 and a host device in the form of a computer 14. As indicated above, in other embodiments, the reader and computer may be combined together in a single device where desired. Other processing devices may utilized as well, such as fax machines, etc. In this embodiment, the memory card 10 and an associated security measure, for example, biometric information stored on memory card 10, may be utilized to verify identity. The memory card 10 may be used in combination with one or more biometric characteristics taken from the user for the purpose of signature verification. The following illustrate some examples in accordance with the present embodiment.

In one example, the memory card 10 and biometric match may be required of a user in order to gain access to a designated device, such as to log onto a given computer. The memory card 10 and biometric match would in essence serve as a password in this embodiment to verify the identity of a user. Access may be denied where a user's identity is not verified. In other embodiments, access to any given computer may be restricted to designated individuals, so that the memory card and associated biometric information would also serve to limit access to only permitted users.

In addition, in accordance with this and other examples, the memory card 10 and biometric match may be required of a user in order to communicate with a recipient, such as electronically over a network, for example, by email, a digital sender, fax or other document in electronic form. As indicated above, where the memory card 10/biometric match is required to log onto a computer, then identity has already been verified and further security measures in order to communicate with a recipient electronically may be optional where desired. Alternatively, if there are no log in security measures or for added security, an electronic communication may further require an authentication mark, to verify the identity of the sender, which may be packaged with a communication sent to a recipient.

The authentication mark in accordance with the various embodiments may be utilized so that it is either visible to the recipient or not, as may be desired. A visible authentication mark, as indicated above, may serve as a signal to a recipient that it is safe to open a document. The presence of the authentication mark, however, irrespective of it being visible or not, may serve as a mechanism for signature verification, as discussed below. The system can be set up, for example, so that a communication will not be sent from a particular computer and/or will be refused receipt by a recipient computer unless an authentication mark is present. Alternatively, it can be arranged so that the sender and/or recipient computers are able to detect the presence of an authentication mark, and then notify the recipient whether or not one exists. Other examples are also possible.

An authentication mark may include a variety of designated information regarding the sender, such as name and location. Location information may be provided via the computer 14, such as a particular internet protocol ("IP") address. In other embodiments, location information may be provided by other means, such as via memory card 10, for example, GPS tracking information may be uploaded from the card 10 to the computer 14 via reader 12. Biometric and/or Name information may be provided from the memory card 10. Other information may also be provided as well where desired, such as time and date stamp from either the memory card 10 or computer 14 or both.

In a transaction, the authentication mark serves to verify the identity of a sender of an electronic communication, and accordingly, may also serve to authenticate the content of a particular electronic communication. For this reason, the authentication mark may function as a form of signature verification or as a substitute for a physical signature, such as in situations requiring a signature to be binding, for example, legal documents, such as contracts, financial transactions, business transactions, etc.

In still another embodiment, a memory card can be used to verify identity of an individual in situations where merchandise or services owed to that individual is desired to be received, such as will call transactions.

Some examples of the various advantages of certain embodiments of the present invention include:

1. Configuration—a storage device, despite its complexity of microchips and printed circuit board interconnections, is configured into a lightweight device, such as a card that can be easily stored in a wallet.
2. a storage device does not require a battery for its operation.
3. Security—data entered via contacts or pins is encrypted and stored. Outgoing data is then decrypted. This can only be done if the contact reader is classified as a reader for that specific data.
4. All data is partitioned or compartmentalized so only certain readers (also referred to as playback/send units) can have access to certain data. For example, if this device were used as a driver's license, a police reader would have access to the digital photo, driving record, arrest or conviction record of the driver.
5. No data can be transferred unless there is a biometric match between the reader (playback/send unit) and the person who possesses the card—such as fingerprint or fingerprints, palm or hand print, retinal match, face print, or DNA screen, as examples.
6. A digitally encrypted picture of the owner of the card.
7. Data from the card is automatically stored in the hard drive of the card-issuing establishment and can therefore be easily replaced by uploading using special software.
8. Ruggedized for protection of internal circuits and microchips.
9. Integration of location tracking technology, such as GPS technology with unique circuitry allowing for exact placement of the card in time and space when it is utilized. This feature can have widespread implication, such as in preventing crime or fraud in multiple industries.
10. Interactive nature—a storage device can be edited as well as unedited.
    The advantage of this feature is reflected in this example: A person visits a doctor. The person presents his card. He or she is biometrically linked to the card so ownership is verified. His or her insurance information and medical information from his or her last encounter with any physician is recorded, as is the time and place he or she was seen. The doctor examines the patient, updates the card through the physicians send/play back unit and writes the patient a new prescription (special software can further assure that the prescription does not interact adversely with other medications the patient is presently taking, can also inform whether the drug is covered by his or her insurance company, and can clearly print the name of the mediation and instructions). The patient then goes to the pharmacy. He or she is again identified via biometrics, his or her card is placed in the pharmacy reader. The pharmacy reader cannot read other information about the patient except items permitted to access. This will primarily be insurance information and the prescription information. This is one example of the interactive nature of the card, although as should be understood, other examples may also be provided.

The interactive nature of the identification card in accordance with embodiments of the present invention may provide any number of the following advantages:

Identification protection through encryption and/or biometrics.

Confidentiality by the partitioned memory and contact system of the play/send functions to allow only information needed for each transaction.

Unique ability to edit based on access to certain portions of the system by certain readers.

Security—no one reader can read all portions of the system

Reduction in medical error—the information on the patient's exam is accessible to all medical specialists in different locations all over the world. The time and place stamp helps with the accuracy and decreases the doctor's need to rely completely on patient recall, which leads to better care and markedly reduced costs to the medical industry (less duplication of test, etc.). Further, prescription error will be eliminated saving lives and money.

Insurance Fraud—people cannot use other people's cards, having enormous implications in Medicaid fraud and health insurance fraud in general.

Prescriptions can be linked to what the insurance formulary will cover—this allows both pharmaceutical and health insurance companies to same money.

11. An identification card may be uniquely treated so that it is resistant to elements and routine mechanical stress. An example of this is flame resistance, water resistance and bend resistance.

12. Contact as well as adaptation to contactless operation between the card, reader and host device.

Some further examples of advantages of still other embodiments of the present invention include:

1. Power source included in the card, such as alkaline, nickel, lithium battery or solar cell, as examples.
2. Location tracking added.
3. Mechanism for emergency contact, such as an E911 feature—this may be a contact feature or a voice recognized feature, as example, responding to words such as "help".
4. Integration capability of Wi-Fi technology to adapt the product through circuit integration to a local area network in a defined region, some examples include blue tooth and 802.11.
5. Integration of digital images through lens and voice transfer through microphone/speaker adaptability.

In accordance with the various embodiments of the present invention, the following is a partial listing of some exemplary application areas:

Police and Law enforcement.
Insurance Industry, including healthcare, pharmaceutical formularies, Medicaid, Medicare, etc.
Medical—Dental records.
Financial such as credit cards, debit cards, bank cards, etc.
Hospitality—such as travel and loyalty points.
Immigration such as student visas.
Government—social security card, homeland security card.
Corporate.
Individual and Privacy Identity Protection.
Entertainment.
Personal use.

In addition, embodiments of the present invention may further include a memory device, such as a stick/chip, which may only record and not have an audio or playback feature directly incorporated into the unit. The separate and detachable memory stick may be programmed to record and document any disruption or removal from the system including logged in and logged out times and dates. Also, the memory stick can have a code that does not allow any changes to be made to the recorded voice without using a unique code, such as, for example, a 12 digit code accompanying the original unit. This will prevent tampering and allow proper documentation of originally recorded voice data. In other embodiments, the memory device may be incorporated within the identification card itself.

The following illustrates in more detail some of the exemplary application areas in accordance with the various embodiments of the present invention.

1. Homeland Security

The following describes one exemplary embodiment in relation to homeland security. In this embodiment, a foreign national enters the United States(or similarly, some other country) and is issued an identification memory card. The card may be encrypted with a digital photograph and other unique identifying biometric data, such as a fingerprint. The entry is permanently time, date and place stamped by indisputable GPS chip in the card. This card can be tracked in real time or traced with each use. Uses in cards for student visas, visitor visas, passports, etc., can be utilized with this technology. The legal record for this individual can be entered into the card, such as the purpose here in the U.S. and who the immediate family members are, etc. This information may be seen only by the proper legal authorities, such as the police, INS, etc. No one else can use the individual's card because of the biometric utilization features. Without the fingerprint, for example, the card is useless and cannot be read. An individual is linked to a particular card. The card may also be tracked where desired. If someone is being sought for illegal activity, as an example, the card will locate them via GPS. If they have discarded the card and are apprehended with someone else's card, the biometrics will not match. If they do not have any card, or a proper card, then their biometric data will reveal their true identity. Law enforcement will have biometric readers that are part of the system to help in this process.

Furthermore, in other embodiments, cards may be utilized as a social security/homeland security card. These cards can provide accurate information that preferably cannot be altered with the exception of authorized government agencies that issue the data. The biometric link to each card verifies the individual of the card as owner and can place the owner at a specific location, date and time. This system provides an unprecedented level of personal identity security and protects society from imposters and criminals wishing to cause harm by using deceitful practices. The social security number for each person can be digitally encrypted and protected by multiple levels of biometric security. This will virtually "identity theft proof" the card. Individuals may also choose if they want the card to be trackable in real time to help them locate it if lost. The universal applications will encourage people to want to have a single memory card as opposed to a wallet full of separate conventional cards.

2. Law Enforcement

The identification card can also be utilized as a driver's license. The added features can include information such as outstanding tickets, prior arrests, etc. Biometrics assures the identity of individuals to authorities. The owner of the card benefits by the secure nature and unalterability of the card. The owner also benefits from the universal applications, one of which will include the insurance information and car registration stored on the card. This will also help in eliminating the possibility that individuals will be issued citations for not having these cards available.

3. Healthcare

One feature of the memory card, besides the safe transfer of medical records and dental records, including x-rays, is fraud prevention. A medical provider may not be able to commit fraud by stating a patient was treated that was not treated since the biometrics and time/place stamping offered by GPS clearly shows the patient was in that location at that time. Further, a health insurance card such as Medicaid or Medicare card cannot be used by anyone but the owner of the card. This will help to prevent unauthorized persons such as unregistered illegal aliens from illegally gaining access to the Medicaid or Medicare system. It will also prevent the illicit receipt of prescription medications. It will ultimately prevent anyone but the authorized owner of the card to derive any health or medical benefits from the card.

4. Financial Transactions

The memory card can be utilized for electronic transactions, including, for example, credit card, debit card and ATM features. Examples would be similar to how these stand-alone cards are used today with a major exception. Personal biometric data is presented at the time the card is used, which will eliminate credit card fraud and theft. For example, no transaction can take place with the card, such as at a department store check-out register, unless the biometric indicators are matched, such as fingerprint. Further, as discussed above, the manner in which the card is designed in certain embodiments will not allow other compartments to be viewed. The reader will only be able to access/verify needed information for the transaction. This might include a catalog of credit card numbers to be chosen from, a photo ID and fingerprint verification, as example. For illustration purposes, pins 1 and 3 are attached to the reader and interfaced with the card, allowing display of the data onto a computer screen, register screen, or handheld reader with LCD. The transaction is permanently time/location stamped by the card itself.

5. Privacy

One of the features of the memory card in accordance with embodiments of the present invention is privacy. No one place or establishment has access to all the identifying information. A merchant or other third party will only have access to designated information. The remainder of the information is protected. The information may also be date/time stamped for added protection as well as tracked where desired.

Depending on use, a memory card may be tracked by an individual and not necessarily any organization. This may be done via a cellular/satellite network and corresponding Internet website. An aspect here is the ability to compartmentalize the data and its use. This allows one card to be used for all features and privacy to be maintained.

The following is another exemplary embodiment of the present invention. In this example, Baby Jane Doe was born on Jun. 2, 2003 at 2:00 AM EST. at Winthrop Hospital in Mineola N.Y. Her physician signed her birth certificate, which was forwarded to New York State for processing. The nurse in the hospital used special ink to mark her hand prints and footprints for the proud parents. A copy was also forwarded to the Social Security Administration. The Social Security Administration issued Jane Doe a card called the DID™ Card. It is a specialized memory card that will be with Jane Doe for the rest of her life. It will store her biographical and biometric information. It will protect her from being the victim of fraud and identity theft. It will help keep her information private as she grows into an adult and through the many facets of the life ahead of her. This new card will help protect her health. It will help prevent medical errors. The card will enable doctors to treat Jane Doe with greater accuracy. It will also help Jane Doe save tens of thousands of dollars over the course of her life. The following illustrates the possible uses of the DID™ card over Jane Does' lifetime.

Jane Doe receives her DID™ card two weeks after she arrives home from the hospital. The DID™ card is preloaded by the Social Security Administration (SSA) with the following information. Name, address, date of birth, SS#, digitally encrypted picture, Digitally encrypted hand print (all of this information can not be edited, erased, rewritten, tampered with or reproduced except by the SSA), digitally encrypted photo of both parents as well as parents fingerprints and retinal print. The remainder of her card is empty storage which will be filled throughout her lifetime. Since Jane Doe needs to see the pediatrician in the first days and weeks of life, it will be necessary to provide health insurance information for her. Jane Doe's DID™ card will already start to be used. The DID™ card is brought to the Insurance Company or to the home computer to link to the insurance company website by Jane Doe's mother. The card is placed in a reader with special contacts between the card and the reader which are only available for "INSURANCE-HEALTH" use. A digitally encrypted picture of Jane Doe, her mother and her father appears on the linked computer screen or LCD monitor at the insurance company. Jane Doe's mother places her thumb into the biometric sensor attached to the reader. The biometric print confirms that this is Jane Doe's mother and Jane Doe is the owner of the DID™ card. Jane Doe's information needed for insurance processing is then downloaded onto the database of the insurance company. The insurance company then downloads all needed insurance information for Jane Doe. The transaction ends. Jane Doe's first stop with her DID™ card is at the doctors office. She enters the office and presents the DID™ card to the office receptionist who places it in a reader. Jane Doe's photo, as well as her mothers and fathers appears on the LCD screen. Jane Does mothers fingerprint is entered via the attached biometric sensor (and retinal biometric as well). The receptionist verifies this is Jane Doe and her mother. The insurance information is then entered via USB port into the database of the doctors office. The exact time and place of the visit are stamped on Jane Doe's DID™ card via unique GPS technology. The "MEDICAL" portion of the card is accessed. The doctor records his findings. The uniquely placed pins only allows certain portions of Jane Doe's DID™ card to be read by the doctors office. The doctor then records his information from today's visit and downloads it onto the card. A typical entry may be as follows: Jane Doe, age 2 weeks. Brought in by mother for well baby initial visit. Infant is healthy. Return in 2 weeks. May 6th 2003, 1248 hours, 394 Old Country Rd. Garden City Nebr. 11 53 0 and Jane Doe biometric downloaded to the doctor's record or medical database.

Jane Doe's subsequent visits can be recorded in a similar fashion. A detailed record of her allergies can be recorded. Her immunizations can be recorded. All her medications can be recorded. If she moves to another state, her DID™ card with all of her information can go with her. If the doctor prescribes medication for her, the prescription can be accurately read from her DID™ card in the pharmacy's reader. Drug interactions can be found before Jane Doe is harmed. Potential allergic reactions can be thwarted. Software which links the medication with the Insurance company formulary can save both Jane Doe and her insurance company money.

As Jane Doe grows her biometric information is updated on a yearly basis. Her medical history is documented. All of her immunizations are kept. Any trip to the emergency room is recorded for all of her doctors to see. Complete with date and time entered permanently into the record. Any visit Jane Doe had to the dentist office is also documented. Her dental x rays are added to her DID™ card for storage under the compartment labeled "DENTAL".

At the age of 12, Jane Doe is going to go on a family vacation to Europe. She must now get a passport to travel. This is perfect for her DID™ card. Jane Doe presents her DID™ card to the passport authorities in the U.S. Her digital photo appears on the screen after the card is placed in its reader. The reader cannot see any sections labeled "MEDICAL" or "DENTAL" to help secure Jane Doe's privacy. Nor can the reader see "INSURANCE HEALTH". Special contacts on the reader will allow certain transactions for this agency. A special section called "TRAVEL" appears on the screen. This only occurs after Jane Doe's fingerprint and retinal scan document that this is Jane Doe's DID™ card. Passport information is downloaded onto the card. The information is stored in the databank of the agency for future use if needed. Jane Doe is now ready for her travel to Europe. Her parents have already purchased the tickets over the internet and downloaded them onto her DID™ card. Of course her biometric authorization was needed to download the ticket from her home computer with attached home reader with special contacts. She now only has to present her DID™ card at the airport with her biometric confirmations to board the plane and enter the European Union countries.

Jane Doe brings her DID™ card to the local DMV. Her identity is verified through the process she has been using her entire life to this point. Her photo is updated. She is given her drivers license which is downloaded directly onto her card. The DMV also adds her car registration and auto insurance information. These are in unique portions of her card known as "AUTOMOBILE-LICENSE", "INSURANCE-AUTOMOBILE", and "AUTOMOBILE-REGISTRATION" These portions can be read in the future by the DMV and local authorities. Any legal convictions or license restrictions will be seen here. Organ donor information can also be obtained. (This information may include the medical data needed for a national matching program to help hospitals communicate faster and find organ matches faster in the event of sudden death—this can be done through interfacing the card with the hospitals computer and national databanks. The card can have things like blood type and HLA matching etc.) All of this information is stored in the databanks of the DMV, which can be linked to hospitals.

One day, Jane Doe loses her DID™ card. She is not worried. She knows that no one can use her card due to the biometric encryption and the sensors needed for the card to work. She then logs onto her computer at home and via the Internet uploads all of her information onto a new DID™ card, including information from DMV, doctor or dentist, etc. She is identified by her biometric data utilizing both a retinal scan, fingerprints, and stored photo. She may wish to keep two DID™ cards in case one is lost in the future. The process of replacing the information is simple and straight forward. Jane Doe is able to replace each compartment as it is needed. The fact that no one place holds all of her information protects her privacy.

Jane Doe became ill one day. She visited her new doctor. The doctor downloaded all of Jane Doe's history onto his database. He examined Jane Doe and decided she needed several medications. Jane Doe was not feeling well enough to go to the pharmacy to fill her prescription. Now she realized how elderly people that cannot get around much must feel. The doctor downloaded the prescriptions to the DID™ card. The time and place stamp was entered automatically by the DID™ card system. When Jane Doe returned home, she went to her Desktop computer. She placed her DID™ card in it's HOME USE ONLY reader which is connected to her computer. She placed her fingerprint on the biometric sensor and the computer confirmed she was the owner of the DID™ card. She downloaded the prescription which was sent electronically to her pharmacy. She added special instructions that said "please deliver". The pharmacist also received Jane Doe's insurance information, allergies, and medical condition. He also received "other medications" notification to compare. The medication the doctor prescribed was not covered by the formulary of Jane Doe's insurance. An alternative was suggested by the preprogrammed software and confirmed with the doctor. Both Jane Doe and her insurance company saved money, and Jane Doe was conveniently resting at home when her medications arrived.

There are numerous other possible uses as well, such as:
Jane Doe gets working papers;
Jane Doe opens a bank account;
Jane Doe gets her first credit card;
Jane Doe uses her DID™ card to cast her first electronic vote online;
Jane Doe goes to college and needs an ID card to get into the clubs and bars;
Jane Doe gets a job and her company uses DID™ cards for security;
Jane Doe juggles all of life's events using—her DID™ card for business, Personal ,travel, security, medical, and dental.

After a full and happy life. At the end of 99 years, Jane Doe dies. Her DID™ card is sent to the Social Security Administration after the Death Certificate has been downloaded. The SSA records Jane Doe's death and discontinues benefits.

In accordance with various aspects of the embodiments of the present invention, an example encompasses a lightweight, easily carried memory identification card for recording information and controlling access to this information. The memory card includes a file system of electronic files on the card, which are automatically detected and recognized by selected authorized readers. The file system is organized so that stored electronic files appear in separate and distinct compartments in the card, so that only authorized preselected readers have access to particular compartments.

Biometric identifying information is imprinted in the card, so that no data can be transferred unless there is a biometric match between a reader and a person assigned to the card and who possesses the card. Biometric identifying information can be a thumbprint, fingerprint, digital face image, retinal image, voice recognition or any others known to those skilled in the art of biometrics, such as DNA sampling. One exemplary device suitable for fingerprint authentication performs both a fingerprint match and pulse detection on the finger itself The memory identification card where desired can also have each compartment requiring a different unique pin code for access thereto. The separate compartments of the memory card may include a compartment containing, for example, medical information relating to the assigned user of the card, wherein the medical information is accessed only by a preselected memory card reader having the unique pin code assigned to the compartment having the medical information. In this manner, the medical information cannot be accessed by other providing institutions, such as banks or government agencies.

The memory identification card can also have a single chip Global Positioning System (GPS) engine, to identify where the card is being used. In certain embodiments, the GPS engine is activated and powered by the memory card reader. In one embodiment the memory card does not need a separate power source, as the GPS information is revealed from flash memory when the card is inserted within the reader.

In another embodiment, the memory identification card has a power source, such as a battery. In one example, the battery may comprise a lithium cell adapted to be recharged by a preselected card reader. Such a battery-powered memory identification card can therefore be enhanced, such as with a microprocessor, RF receiver, and RF transmitter, for receiving and transmitting wireless telecommunications.

The memory identification card may also display a photo image of the person assigned to the card. In connection therewith, in one embodiment the memory identification card contains in a compartment a digitized photo image of the person assigned to the card, so that the exterior of the card will always bear the internally digitized image. A forger of the image on the exterior of the card will not be able to use the card. In addition, for fraud prevention, one of the compartments may contain biometric identifying information about the assigned user of the card.

The memory identification card also may have a button for initiating a call, such as to 911, and sending a prerecorded message with a request for emergency medical or other assistance. Such an embodiment can also provide the location of the memory identification card.

The memory card may also have the capability to be integrated with an apparatus for taking, storing and transmitting digital images, such as a digital camera.

Moreover, the memory identification card may have an integrated or detachable memory stick/chip adapted to be programmed to record and document any disruption or removal of the card from an authorized user system.

As an alternate feature, the memory card may have a recorder integrated or attached to the card for storing real time voice data into the memory. In addition, security can be included to restrict access to the stored information, for example, wherein the recorded voice data can only be played back by access to a preselected reader.

In addition, the memory card can include an automatic voice notebook, wherein the card is embedded with a real-time clock for time stamping recorded voice segments.

Further, when the card has the recording capabilities, the recorder can have a connector to interface with a preselected reader, having the capability to playback the data signals stored on the memory identification card.

In certain embodiments, the memory identification card is part of a system for storing information unique to a particular person and using this information, for example, for identification, medical, security, insurance, entertainment, hospitality, financial and law enforcement purposes. Such embodiments may include one or more of the following features:

a) a central establishment for collecting and storing the information;

b) lightweight, memory card to be carried by the person for recording information downloaded from the actual establishment, wherein the card includes:

i) a file system of electronic files on the card which are automatically detected and recognized by selected readers, and the file system is organized so that stored electronic files appear in separate and distinct encrypted compartments; and ii) biometric identifying information on the card so that no data can be transferred unless there is a biometric match between a reader and a person assigned to the card who possesses the card; and c) preselected card readers programmed to extract information from the memory card from specific compartments, wherein each preselected reader has a unique pin code associated with a particular compartment on the memory identification card, so that a preselected reader can only extract information from a compartment for which the preselected reader has the proper pin code associated with that compartment.

Embodiments of the present invention also include a method of verifying the identity of, and extracting information about a person. In an exemplary embodiment, the person carries a memory card in which is stored identifying biometric information about the person, wherein this information is preferably stored in a compartment separate from other compartments on the card. The person submits the memory card to be scanned by a reader for identifying purposes, and the card reader has a unique pin code, which allows access to the encrypted compartment on the card.

Thereafter, an operator of the card reader compares the accessed biometric information with biometric information taken directly from the person having the memory identification card.

In addition, the memory identification card may contain other encrypted compartments, each of which includes a different bundle of information, such as medical, security, insurance, entertainment, hospitality, financial, travel, general business and law enforcement purposes, to name a few, and each compartment may further have a different unique pin code for access thereto.

Figure 2:
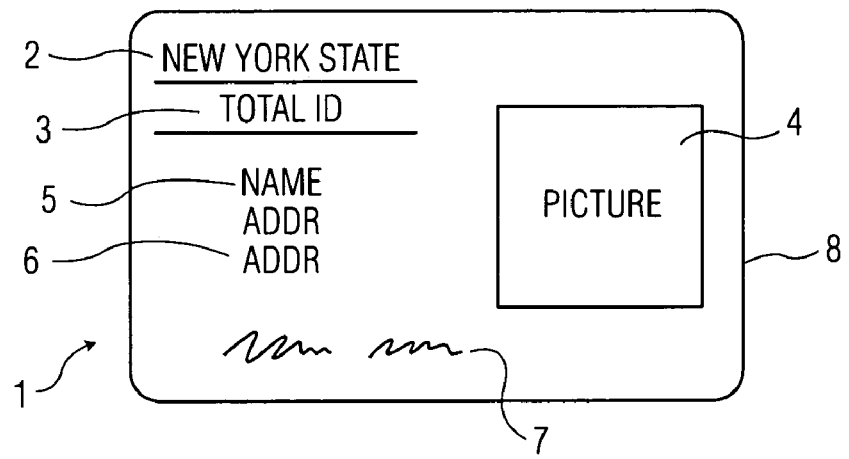
FIG. 2 is a front view of an embodiment of an identification card of the present invention.

FIG. 2 illustrates an exemplary memory card and associated system and method in accordance with an embodiment of the present invention. In this embodiment, card 1 comprises a smart card or integrated circuit type of device, which is described in further detail below. In other embodiments, card 1 may be of other types as well, such as a magnetic strip card, as an example. As shown in FIG. 2, card 1 includes an exterior picture 4 of the card holder, an identification of the issuing agency 2, card logo 3, name of cardholder 5, address 6, and signature 7. In other embodiments, various combinations of the foregoing elements may be utilized rather than all of the elements, and further, additional or alternative substitute elements may be utilized as well, where desired.

The card 1 in accordance with the present embodiment further comprises a linear array of input/output (IO) contacts 8, which are located at one end.

Figure 3:
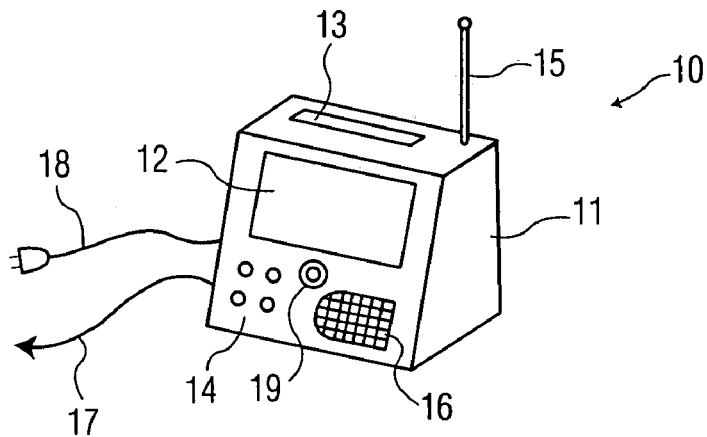
FIG. 3 is a perspective view of an embodiment of a transmitter/receiver unit (T/R) of the present invention, which interfaces with an ID card.

Card 1 interfaces with an exemplary embodiment of a transmitter/receiver (T/R) unit 10 shown in FIG. 3. Socket 13 accepts contacts 8 of card 1. Housing 11 contains the power supply and electronics for this interface unit which is connected to an AC line power 18 and via a cable 17 to a host computer, which can be a personal computer (PC) or a point of sale (POS) unit. Transmitter/receiver (T/R) 10 has a liquid crystal display screen 12 and function buttons 14. Two biometric devices, such as, for example, thumb print scanner 16 and the lens 19 of a digital camera, are shown. However, a single biometric indicator can also be used, as well as a suitable plurality of biometric devices. The digital camera can support facial scanning of the customer. If other biometric techniques are used, they may be supported by an input device as part of T/R 10. A different lens 19 can support retinal scanning, while a cell sampler with its attendant hygienic support accessories can support DNA identification. Antenna 15 is used by an ID card 1 to support its internal GPS receiver.

Figure 4:
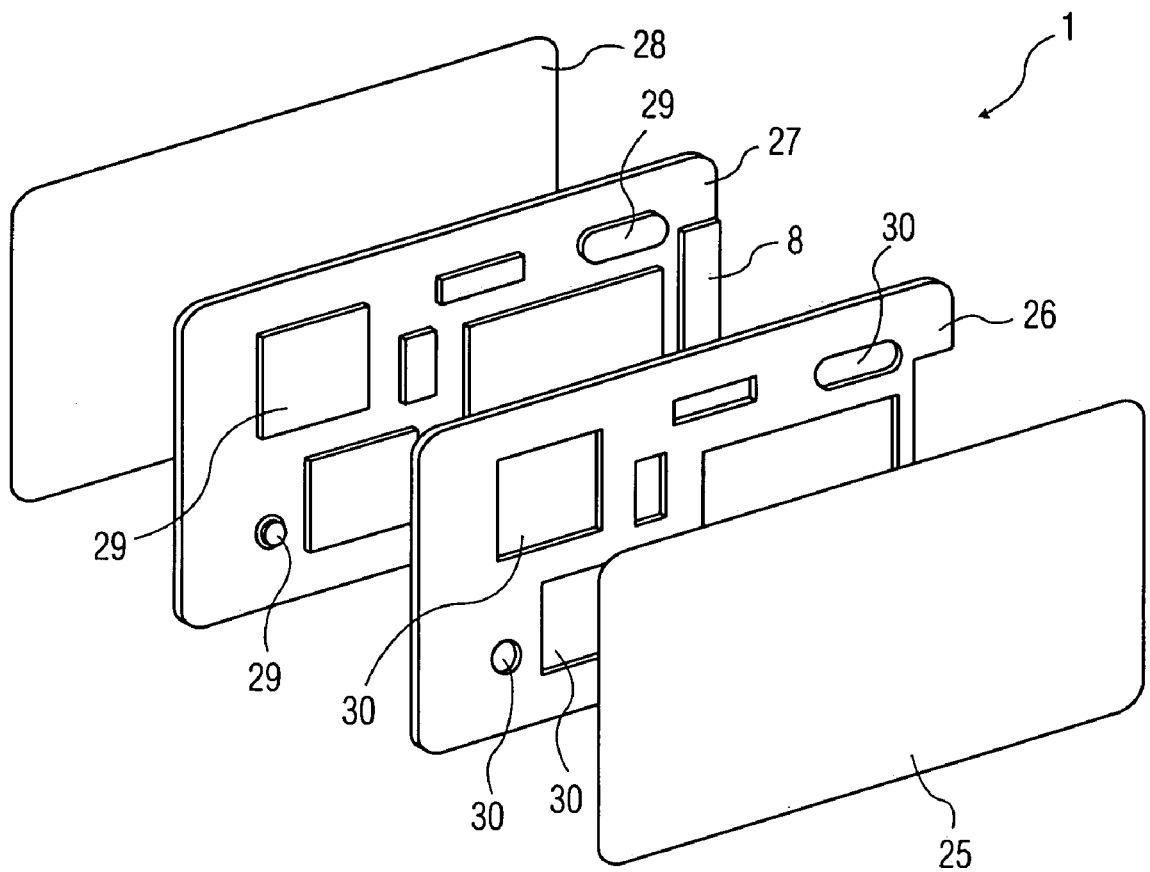
FIG. 4 is an exploded perspective view illustrating four major layers of an embodiment of a digital ID card of this invention.
Figure 5:
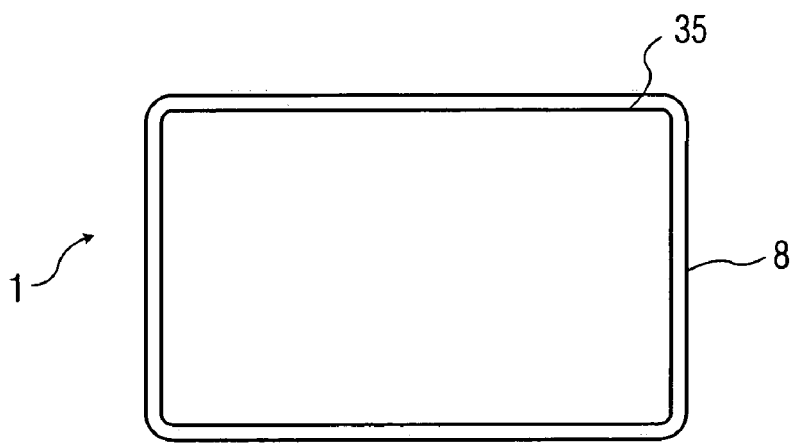
FIG. 5 is a front elevational view of an embodiment of a digital ID card using a stiffening frame.

ID card 1 is a ruggedized unit with care being taken to resist bending and to be scratch, water, and flame resistant. FIGS. 4 and 5 relate to the physical structure to assure this robustness. While other suitable configurations may be used, FIG. 4 shows a four layer laminated structure consisting of front layer 25, stiffener layer 26, printed circuit board (PCB) layer 27 and back layer 28. The laminated structure permits each layer to be functionally optimized. For example, front 25 and back 28 layers are selected to be amenable to high quality indicia application, scratch resistant, and flame resistant. In fact, these two layers themselves can be laminates of two separate layers with additional coatings. Printed circuit board (PCB) 27 has certain electrical characteristics which facilitate high quality conductive traces on a substrate of known low-loss dielectric. Components 29, which are integrated circuit modules and discrete active and passive devices, preferably have a low height to minimize card thickness. Input/output (IO) pin socket 8 is also preferably low profile.

After the PCB 27 is populated, it may be coated with a moisture resistant conformal coating. Urethane, acrylic, and silicone spray coatings are available, but they cannot match the preferred parylene coating usually reserved for medical and military electronics. In one embodiment, the thickness of stiffener layer 26 is equal to the height of the highest component 29 (including socket 8). Holes 30 shaped to components 29 and in registration with them may be cut through, so that layer 26 does not add any thickness to card 1. The preferred material of layer 26 is a two-sheet laminate of oriented carbon fiber material wherein the fibers of each of the two layers are orthogonal to each other. An optional stiffening and edge protection aid may be provided by frame 8 shown in FIG. 4. This encircles card 1 in a titanium frame that also rigidly engages socket 8.

Figure 6:
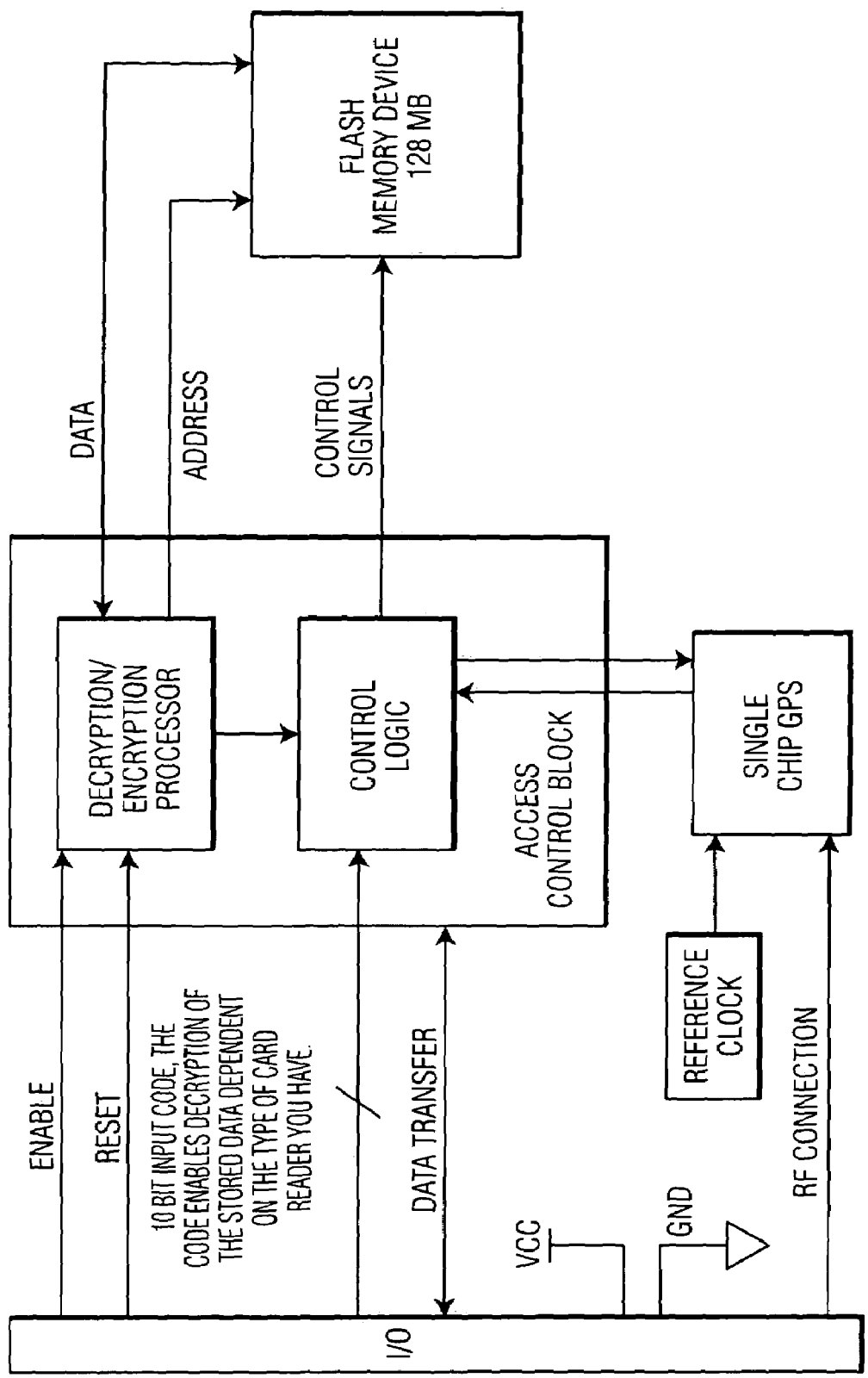
FIG. 6 is a block diagram of another embodiment of an ID card in accordance with the present invention.

FIG. 6 is a block diagram of the non-powered embodiment showing 128 MB flash memory with all of the on-board data. An access control block implemented as a microcomputer or digital signal processor (DSP) controls all operations as well as functioning as a decryption/encryption processor. Power, data transfer, control and RF GPS connection are all interfaced through the input/output (IO) connector. A single chip GPS receiver such as, for example, the "Instant GPS" assisted global position system receiver commercially available from Motorola® is small enough to fit into a wristwatch.

Figure 7:
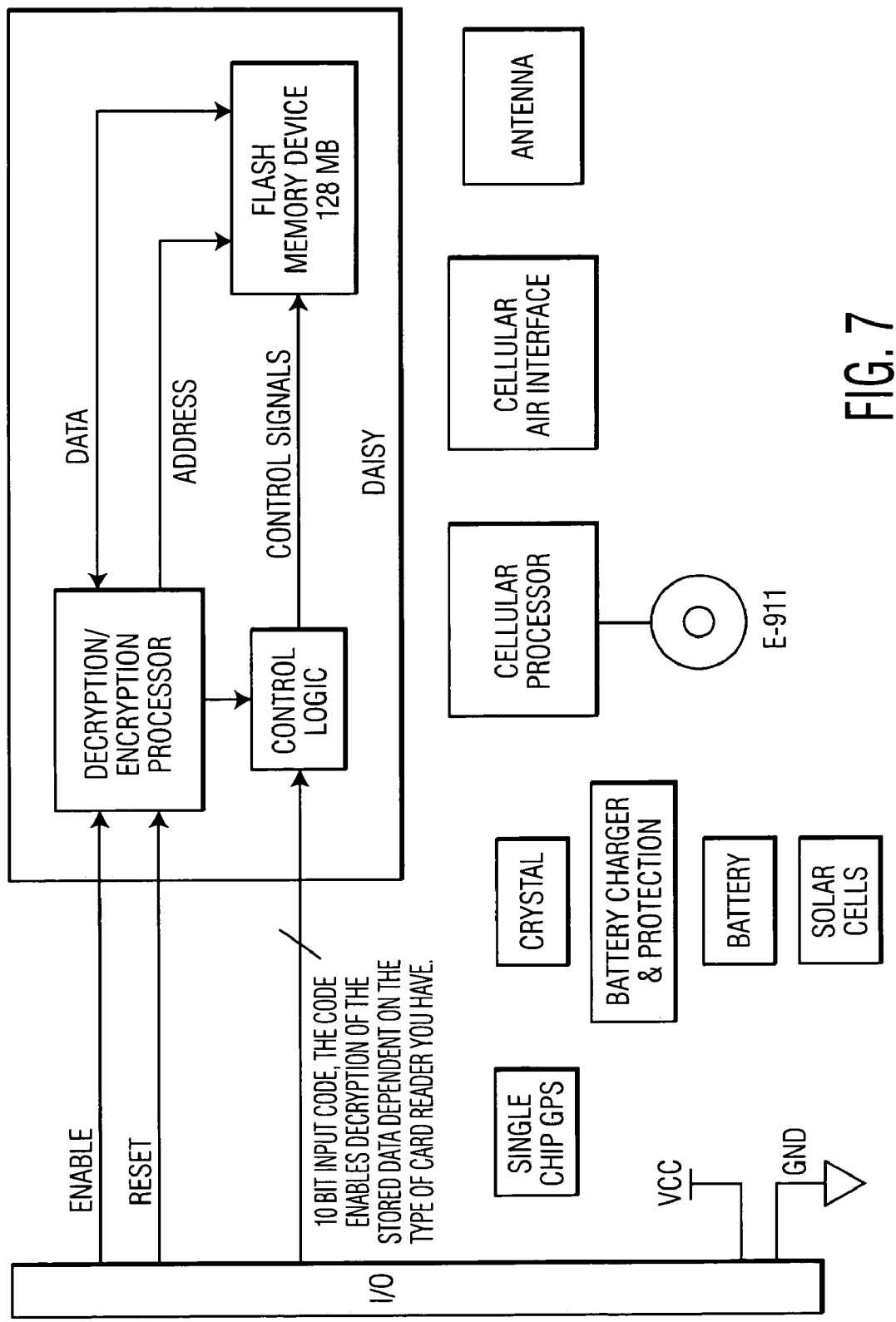
FIG. 7 is a block diagram of another embodiment of an ID card in accordance with the present invention.

FIG. 7 is a block diagram of a battery powered embodiment of the ID card. Note that several functional blocks have been added to the non-powered platform in this battery powered embodiment. Most notable are the battery, battery charger, solar cells, and cell phone functional blocks with antenna. The battery is charged via power from the IO socket. The cellular processor may also have an E-911 function which is engaged via a repetition of a keyword such as "HELP" or by pressing an area on card 1 which has an embedded strain gauge which functions as a switch (shown as "E-911").

The GPS also has its antenna on-board in the powered embodiment. The solar cells are used to extend the required charge interval and in case the card is lost. Solar cells are placed on both front and back for this eventuality. If a card is dropped on the ground and has access to sunlight or bright artificial lights, it can slowly charge a depleted battery (regardless of the side it lands on) to permit a short burst transmitting its location coordinates. This periodic transmission protocol can be initiated after a pre-programmed timeout. Note that even with a battery powered card, the transmitter/receiver (T/R) can be constructed so that it supplies power during a transaction procedure, so that even a battery powered card with a totally depleted battery can be used at any time with a transmitter/receiver (T/R) recorder unit.

Figure 8:
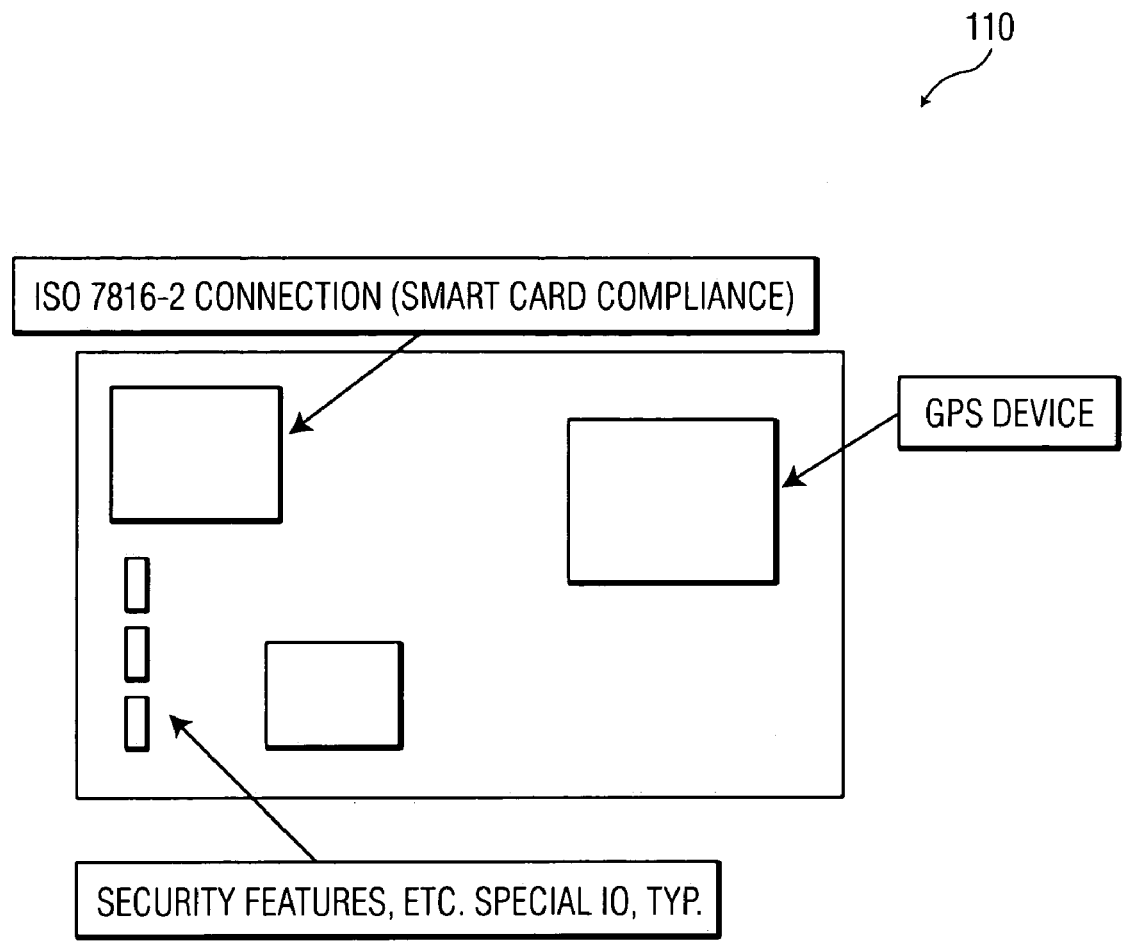
FIG. 8 is a top perspective view in block diagram form of another embodiment of an ID card in accordance with the present invention.

In FIG. 8 is illustrated another exemplary embodiment of a memory card 110 in accordance with the present invention. In this embodiment, card 110 is comprised of plastic, and laminated using layers of polyimide laminate. As should be understood, however, the card 110 in other embodiments may be comprised of other materials and may or may not be laminated where desired. The card 110 further includes in the present embodiment a plurality of integrated circuits which range in functionality from flash memory devices up to smart microprocessor chips with integrated logic, security functions, etc. In addition, a power source is provided comprising a solar cell in the present embodiment, which is utilized for charging and operation of a real time clock. An antenna is provided to enable telemetric data transmission. One example is a foil antenna. Another example is a ceramic antenna.

Figure 9:
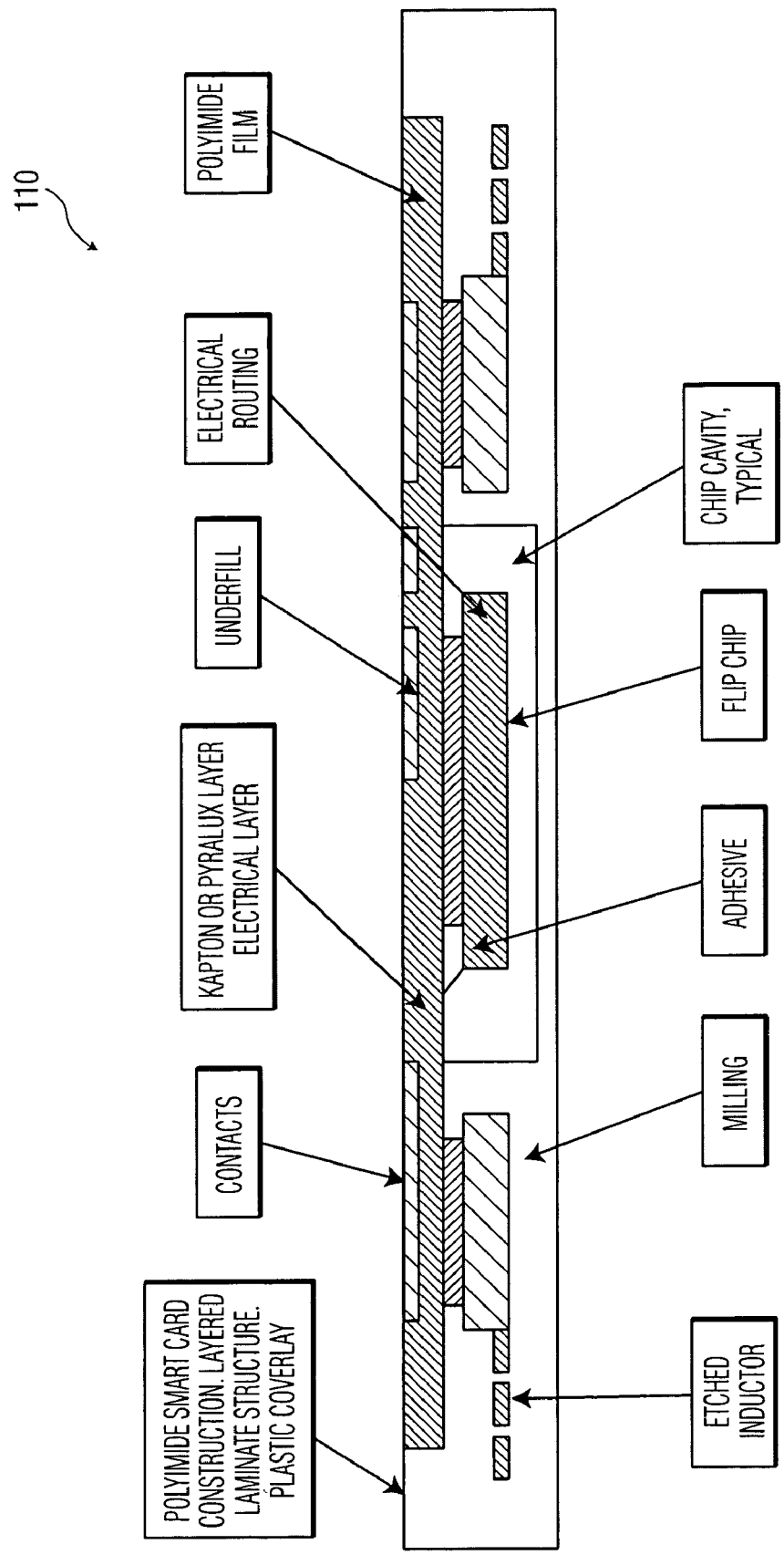
FIG. 9 is front elevational view of the ID card of FIG. 8.

FIG. 9 shows a schematic of an exemplary assembly of the card 110, including electronic packaging, The card 110 may use flip chip parts in certain embodiments where desired. In addition, in certain embodiments, a very small total thickness of the assembly may be realized, such as being as thin as 760 $\mu$m. In some embodiments, card thickness may be minimized to under 2 mm. Further, in certain embodiments, to obtain small dimensions, the use of chips with ⅓ the thickness of regular chips may be utilized.

As shown in FIG. 8, in the present embodiment, the card 110 is illustrated having a nominal dimension of 85.60× 53.98×0.76 mm, although as should be understood, other dimensions may also be utilized where desired. The demanded mechanical properties (bending, torsion, etc.) in the present embodiment are specified in ISO 10536. ISO 7816 contacts are provided in this embodiment as well as specific IO contacts for security purposes. One or more integrated circuits are contained in flip chip cavities on a polyimide substrate in the illustrated embodiment. In the present embodiment, the card 110 is substantially, and preferably, entirely constructed of polyimide laminates with plastic overlays. In other embodiments, other materials may also be utilized where desired.

An onboard GPS may be provided in the present embodiment as well as an antenna. A printed foil antenna is one example. An antenna foil with etched inductivity may be utilized and incorporate, as an example, a 50 or 75 micrometer polyimide foil with 17.5 um or 35 um Cu metallization, The foil may have plated through-holes to accommodate one or more contacts, such as the second contact of the inductivity.

In accordance with various embodiments, the card may be assembled using different processes. In general, the assembly may influence the price of the card, but the required functionality may be provided using various different assemblies, The selection may be influenced by the compatibility to the available production equipment.

There may be certain advantages of the card illustrated in FIG. 8 as compared to a possible alternative solution of mounting the chip directly onto the antenna foil substrate, including:

The chip does not go through the foil lamination process. This eliminates exposures that can enormously stress the chip.

The chip embedded in the same plane as the foil itself provides for a thinner package.

The package being symmetric with the same cover foil thickness on the top and rear provides for a smooth card surface. As a result, etching, embossing and/or high quality printing can then be utilized.

The assembly of the chip carrier module may be standard chip on board construction, which means that the insertion process may be straightforward and can utilize standard industry tooling.

Figure 10:
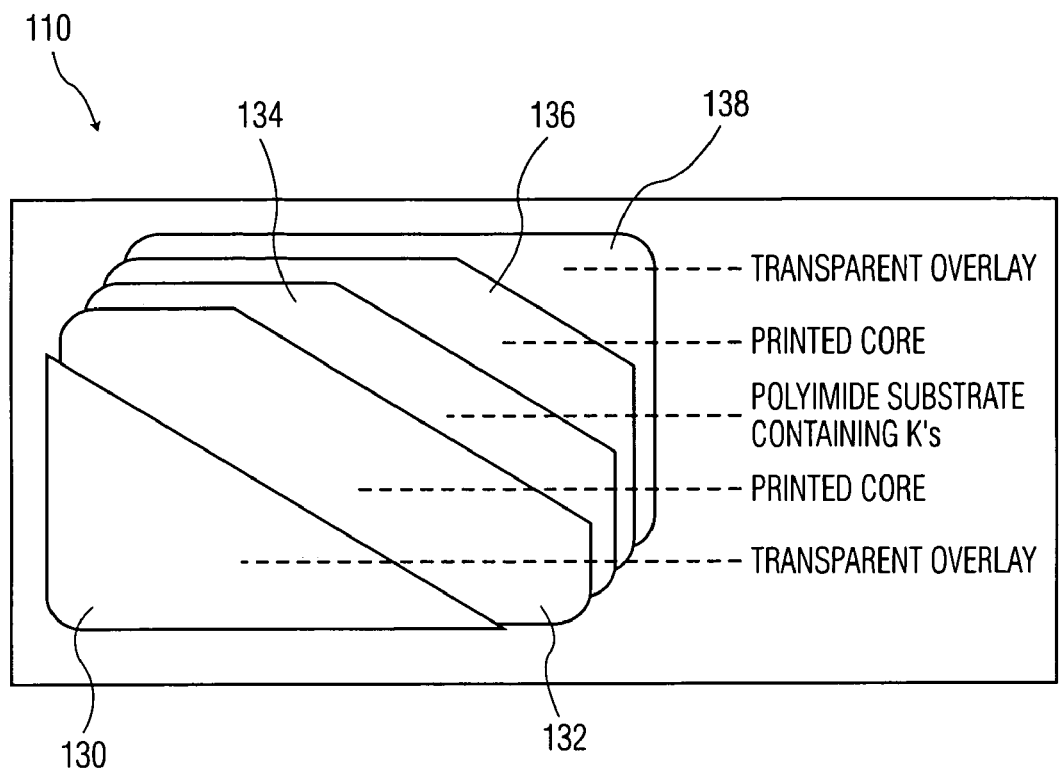
FIG. 10 is an exploded view, partially in section, of the ID card of FIG. 8.

As shown in FIG. 10, in accordance with the present embodiment, the card 110 comprises a plurality of layers, similar to the card 1 shown in FIG. 4. In the present embodiment, card 110 comprises a five layer structure including a front transparent overlay 130, a front printed core 132, a polyimide substrate 134 containing integrated circuits, a back printed core 136 and a back transparent overlay 138. In this embodiment, assembly of the card 110 is based on a module carrier with the chip bonded as a flip chip. In flip chip mounting, the pads of the chip, such as a silicon chip, are directly connected with the contact areas of a lead frame. For this procedure, the chip is 'flipped' over, The flip chip module is inserted into a cavity in the card body after lamination. The size, the position of the module and the relief printing often place restrictions on the placement and size of the coil and module, The mounting of the flip chip module in ISO position is arbitrary but allows the use of standard chipcard manufacturing equipment. In this way, the flip chip module and the card can be produced in single processes.

In this embodiment, the module will not become exposed to lamination stress. If production failures occur, the value of the single defective parts is restricted. In wire bonding, the chip is connected to the interface routing by wires. Wire bonding requires special bonding equipment and therefore requires significant numbers for an economic production. However, flip chip mounting pushes the lower limit, such as to about 1000 pieces, Wire bonding used as a joining technique to electrically contact the chip challenges the thickness that the card can achieve. In the illustrated embodiment, the lower the profile the better. In other embodiments, however, wire bonding may also be utilized.

Flip-chip technology with electrical conductive adhesive is a presently preferred embodiment for mounting and electrical contacting the integrated circuit chips. An advantage compared to the standard technology of wire bonding is easier compliance to minimum assembly height, The adhesive bonding process is preferred to solder flip-chip due to less process steps, simpler bonding equipment and a lower process temperature. A higher reliability is also possible with high purity, high bond strength adhesives compared to solder flip chip, because the remains of the flux used for soldering may form electrolytes and may cause debonding of the underfill material. In alternative embodiments, however, soldering may also be utilized where desired. Pyralux® and Kapton® are some examples of polyimide type materials that may be utilized in accordance with the various embodiments of the present invention.

Figure 11:
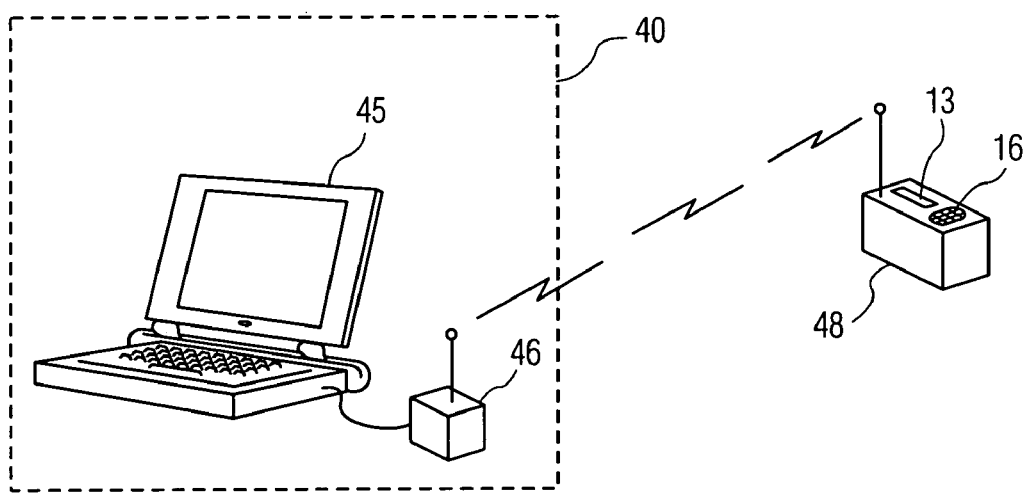
FIG. 11 is a perspective view of an embodiment of a local wireless transmitter/receiver (T/R) unit adapted for police vehicle use.

FIG. 11 shows the use of an exemplary transmitter/receiver (T/R) reader 48 with local wireless communication. This may be used, for example, by police to communicate with a laptop 45 which is within police cruiser 40. Communication transceiver 46 enables this local RF link such as Bluetooth. Transmitter/receiver (T/R) reader 48 is preferably hand carried to a stopped individual in his own vehicle, so that a digital ID card can be inserted in socket 13 and thumb print read by scanner 16. In a traffic violation situation, for example, police may not want the driver of a stopped vehicle to exit their vehicle for security reasons.

Figure 12:
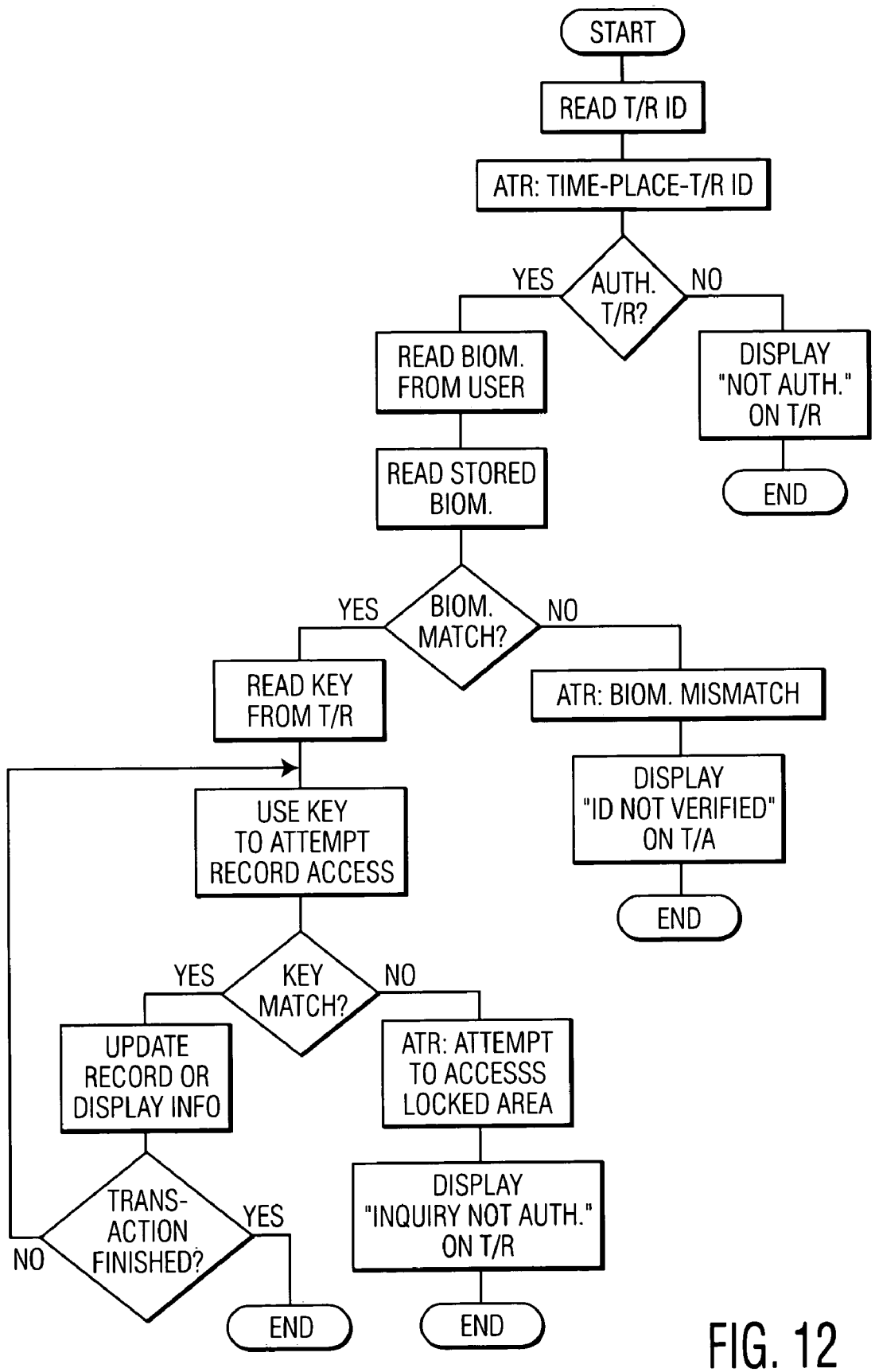
FIG. 12 is a flow chart of an exemplary transaction process using a digital ID memory card of the present invention.

FIG. 12 is a simplified flow chart illustrating an embodiment of the operations internal to a digital ID card of the present invention when attached to a T/R in pursuit of a transaction of some sort. Note that at many juncture, a short record is added to the Audit Trail Record file to be able to retrieve a chain of events in a case of attempted identity theft or other nefarious endeavors.

At the start of the procedure, the transmitter/receiver (T/R) ID number is read and immediately entered into the audit trail with time/place ID generated with the aid of GPS. If the transmitter/receiver (T/R) reader is not authorized to handle transactions on this type of digital identification memory card, a message is displayed on the transmitter/receiver (T/R) reader and the transaction is terminated. Next, the biometric data is read from the user via the T/R and compared with the encrypted data on the digital identification memory card. If there is support for an auxiliary procedure (not shown), at this point, the encrypted picture of the customer can be displayed on the transmitter/receiver (T/R) reader for visual comparison with the picture on the face of the digital identification memory card and with the face of the customer. (Similar signature comparisons can also be performed). In any case, if there is no biometric match, the transaction is stopped, otherwise the transaction continues. Each access of a data record must be mediated through a match between a transmitter/receiver (T/R) reader key and one that controls access to the particular data record. Although not shown in this simplified transaction flow chart, some transactions will permit a customer to waive security on a particular data item, but this event too will show up in an audit trail record.

Figure 13:
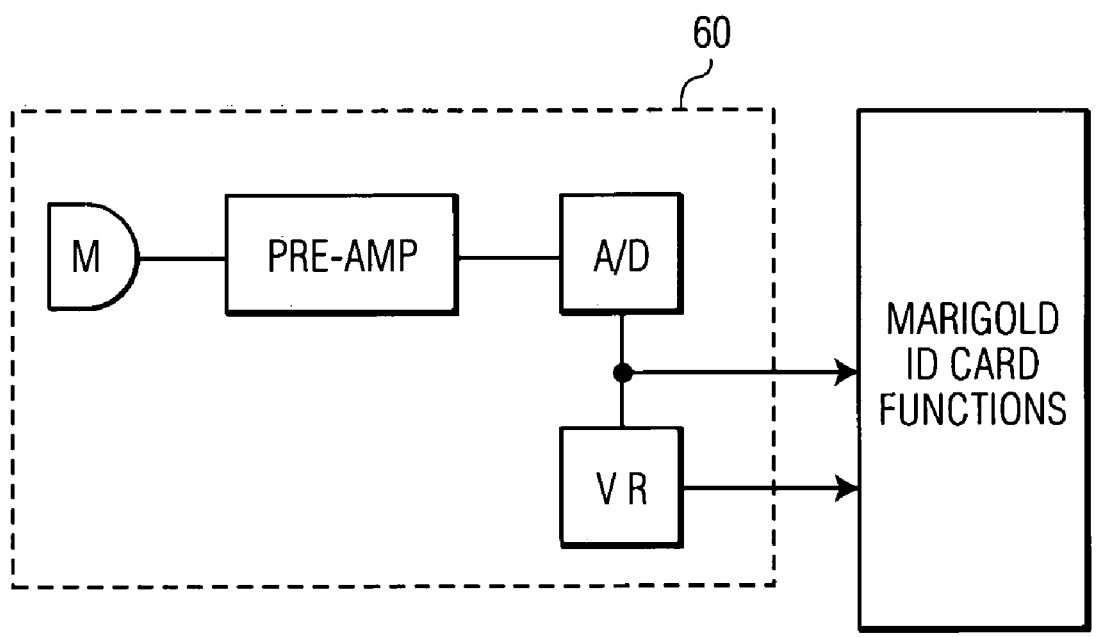
FIG. 13 is a block diagram of exemplary audio enhancements to the embodiment of an ID card of FIG. 7.

FIG. 13 shows an alternate embodiment for an identification card of the present invention with audio capabilities. In one embodiment, an optional dictate only recorder with remote encrypted playback is provided in the card. The enhancements 60 to the digital identification memory card include condenser microphone M, preamplifier, analog to digital converter (A/D) and voice recognition (VR) software running on one of the digital identification memory card. The voice recognition feature is coordinated with its GPS, so that one can input a specific geographic address and it will be plotted on an LCD screen. The audio features can input information, such as recipients of phone calls. The record-only recorder is incorporated into the thin card, so that a user access his or her digital identification memory card and he or she could dictate anywhere such transactions as:
  a) "Deduct $78 for dental bill from my checking account to Dr. Jones"
  b) "Took diabetes medicine now at noon"
  c) "Schedule motor vehicle exam"
  d) "Purchase radio from XYZ Corporation from my VISA account and tell UPS to ship it to Main Street by UPS Ground"
  e) (from traffic judge) "Enter three points on card recipient's drivers license for traffic violation"

All of the above transactions (encrypted and time stamped) could then be downloaded into a playback unit similar to transmitter/receiver (T/R) unit 10 of FIG. 2. Transmitter/receiver unit T/R 10 is enhanced with audio reproduction capability. Screen 12 can be used to display map or other visual indicia. For more appropriate capability in this mode of use, transmitter/receiver unit (T/R) 10 may be adapted to be used portably in a motor vehicle by converting AC power line 18 to a vehicle-connected DC power input. In a further alternate embodiment, the digital identification memory card can be temporarily used as a cell phone.

It is further noted that other modifications may be made to the invention, within the scope of the approved claims. Accordingly, it is intended that the invention not be limited to the specific illustrative embodiments, but be interpreted within the full spirit and scope of the appended claims and their equivalents.

I claim:

1. A memory card comprising:
  one or more storage devices for retaining information;
  an interface mechanism for transferring information either from or to the one or more storage devices, wherein the interface mechanism comprises one or more physical contacts located on the surface of the memory card, and with the one or more physical contacts being in connection with the one or more storage devices, the one or more physical contacts further being adapted to engage an external device;
  a security mechanism for regulating access to the information retained in the one or more storage devices, wherein the security mechanism comprises a specific arrangement of the one or more physical contacts of the interface mechanism, with the memory card being adapted to transfer specific types of information based on a corresponding physical connector associated with the external device; and
  a tracking mechanism for associating the physical and temporal location of the memory card with the external device, wherein said tracking mechanism is activated by the external device.

2. A memory card of claim 1, wherein the interface mechanism comprises a transmitter/receiver.

3. A memory card of claim 1, wherein the interface mechanism comprises an antenna.

4. A memory card of claim 3, wherein the antenna comprises at least one of a foil antenna or a ceramic antenna.

5. A memory card of claim 1, wherein the security mechanism comprises biometric information stored in the one or more storage devices and adapted to be compared via the interface against actual measured biometric information.

6. A memory card of claim 1, further comprising one or more integrated circuits mounted on a substrate as a flip chip.

7. A memory card of claim 6, wherein the substrate comprises a polyimide substrate.

8. A memory card of claim 6, wherein the integrated circuits are mounted by an adhesive.

9. A memory card of claim 1, further comprising one or more layers of a polyimide laminate.

10. A memory card of claim 1 further comprising a power source.

11. A memory card of claim 1 wherein the power source comprises a solar cell.

12. A memory card of claim 1, wherein the tracking mechanism comprises a GPS device.

13. A memory card of claim 1 further comprising a photo image of a person assigned to the card displayed on an outer surface of the card.

14. A memory card of claim 1 in which said card contains in a storage device a digitized photo image of the person assigned to said card.

15. A memory card of claim 1 in which one of the storage devices contains biometric identifying information about the assigned user of said card.

16. A system for storing information unique to a particular person and using said information for a plurality of purposes comprising:
  a) a central establishment for collecting and storing said information;
  b) a memory card for recording information downloaded from said establishment, said card having:
    i) a plurality of storage elements for recording said information in a plurality of different compartments; and
    ii) biometric identifying information stored on said card in one of the storage elements so that no data can be transferred unless there is a biometric match between the stored biometric identifying information and a person assigned to said card;
  c) a plurality of preselected readers for transferring information between said establishment and said memory card; and
  d) an interface between the memory card and the plurality of preselected readers for controlling the transfer of information between the memory card and the plurality of preselected readers, the interface comprising a plurality of separate groups of physical contacts located on the surface of the memory card, with each group of physical contacts being in connection with a different storage element on the memory card, wherein each group of physical contacts comprises a specific unique arrangement of physical contacts different from any other group located on the memory card, with each preselected reader having a unique arrangement of physical connectors located thereon which are configured to match the specific unique arrangement of physical contacts of designated ones of the groups of physical contacts located on the memory card, so that a preselected reader can only extract information from a compartment for which said preselected reader has the corresponding physical connectors associated with that compartment.

17. A system of claim 16 in which said biometric information includes a digitized photo image of the person to whom said memory card pertains.

18. A system of claim 17 in which said memory card display a picture of said person for comparison with the digitized photo image of said person.

19. A system of claim 16 in which said memory card contains a single chip GPS engine allowing said establishment to track the movements of said memory card.

20. A method of securing information on a memory card comprising:

accessing one or more establishments via an interface mechanism; verifying the identity of the card owner by comparing identifying information stored on the memory card against identifying information stored in an external device, wherein the interface mechanism comprises one or more physical contacts adapted to engage a corresponding physical connector associated with the external device;

transferring selected information between the one or more establishments and the memory card when the identity of the card owner is verified, wherein the selected information is based on the specific arrangement of the physical connector associated with the external device.

21. The method of claim 20, wherein the identifying information comprises biometric information.

22. The method of claim 21 in which said biometric information comprises one or more characteristics selected from the group consisting of facial characteristics, finger prints, DNA, and retina characteristics.

23. The method of claim 21 wherein information is transferred from said one or more establishments and downloaded onto the memory card when identity has been verified.

24. The method of claim 23 wherein the information stored on said card is encrypted.

25. The method of claim 24, wherein the memory card comprises multiple compartments, each of which includes a different bundle of information, with said biometric information being stored in one compartment, each compartment having a different unique physical contact for access thereto.

26. The method of claim 25 further comprising providing location information for allowing the memory card to be tracked.

27. The method of claim 26, wherein the location information comprises GPS tracking.

28. The method of claim 27, further comprising a GPS engine for providing the GPS tracking and with the GPS engine located on one of the memory card or a reader for communicating with the memory card.

29. The method of claim 28, wherein the memory card comprises a specific arrangement of physical contacts for communicating with the reader, with each reader including a corresponding physical connector for communicating with specific compartments on said memory card.

30. The method of claim 29, wherein said card includes a digitized photo image of the person to whom said memory card pertains.

31. A system of claim 30 in which said memory card displays a picture of said person for comparison with the digitized photo image of said person.

32. The method of claim 29, wherein said biometric information stored on said card is represented by a number.

33. The method of claim 32, wherein an account number is provided on said card that is different than said number corresponding to said biometric information stored on said card.

34. The method of claim 29, wherein biometric information stored on the memory card is unalterable.

* * * * *